United States Patent [19]

Suga

[11] 4,114,813
[45] Sep. 19, 1978

[54] THREE-DIMENSIONAL ATOMIZING SPRAY TOWER

[76] Inventor: Shigeru Suga, Yoyogi 5-20-2, Shibuya-ku, Tokyo, Japan

[21] Appl. No.: 807,325

[22] Filed: Jun. 16, 1977

[51] Int. Cl.² .......................... G01N 17/00; B05B 1/00
[52] U.S. Cl. ..................................... 239/500; 239/505; 239/514; 239/553.5; 239/562; 73/61.2
[58] Field of Search .............................. 239/499–501, 239/504, 505, 513–515, 553.5, 562; 73/61.2, 86

[56] References Cited

U.S. PATENT DOCUMENTS

| | | | |
|---|---|---|---|
| 1,780,168 | 11/1930 | Burmeister | 239/553.5 X |
| 1,996,098 | 4/1935 | Chase | 239/500 X |
| 2,321,431 | 6/1943 | Somes | 239/553.5 |
| 2,489,952 | 11/1949 | Boudreaux et al. | 239/515 |

FOREIGN PATENT DOCUMENTS 60,290 5/1976 Japan.

Primary Examiner—Robert W. Saifer
Attorney, Agent, or Firm—Wenderoth, Lind & Ponack

[57] ABSTRACT

A spray tower for use in spraying a liquid, particularly a corrosive liquid which is used to test the corrosion resistance of test samples, includes a vertically extending cylinder having an open upper end. Liquid is injected into a lower portion of the cylinder, and a gas is injected thereat to atomize the liquid and cause it to pass upwardly through the cylinder toward the open upper end thereof. The cylinder has extending therethrough, in at least one position intermediate the open upper end thereof in the atomizer, a plurality of ports. A deflector member is mounted above the open upper end of the cylinder for deflecting outwardly therefrom atomizing liquid which exits from the open upper end. A directing member is mounted within the cylinder adjacent the ports to direct a portion of the atomized liquid passing upwardly through the cylinder outwardly through the ports. Shield plates are vertically adjustably mounted to the exterior of the cylinder and are vertically movable between a blocking position blocking a portion of the ports and an open position unblocking the ports. There is also provided an uppermost shield plate which is vertically movable to close a portion of a gap formed between the open upper end of the cylinder and the deflector member.

25 Claims, 10 Drawing Figures

4,114,813

THREE-DIMENSIONAL ATOMIZING SPRAY TOWER

BACKGROUND OF THE INVENTION

The present invention is directed to an improved spray tower for spraying a corrosive test liquid onto test samples within a test chamber.

In known arrangements of this type, a plurality of test samples are positioned within an enclosed test chamber. A spray tower is located within the test chamber and a corrosive liquid is atomized therein and sprayed therefrom onto the surfaces of the test samples to determine the resistance of the test samples to corrosion by the test liquid.

In this conventional type of device, the test liquid is sprayed from the top of a vertical tube and is deflected therefrom by a deflector outwardly and downwardly onto the test samples. This type of arrangement works well with basically flat test samples. However, when the test samples have irregular and complicated configurations, it is difficult if not impossible to spray the test liquid onto certain of the surfaces of the test samples. Thus, when the test samples are of a complicated and irregular configuration, it is difficult to obtain test results which accurately indicate the corrosion resistance of the entire test sample.

Accordingly, it has been the practice, when testing complicated and irregularly configured test samples, to avoid the use of a spray tower and rather to manually spray the test liquid onto all surfaces of such irregularly configured test samples. However, such an arrangement is not only time consuming and inconvenient, but also results in atomizing air directly contacting the sample, thereby spreading or diluting the amount of test liquid actually applied to the surfaces of the test sample.

SUMMARY OF THE INVENTION

With the above discussion in mind, it is a primary object of the present invention to provide an improved spray tower for spraying test liquid onto surfaces of test samples located within an enclosed test chamber, whereby it is possible to cover surfaces of irregularly and complicated configurated test samples which do not face upwardly.

It is a further object of the present invention to provide such a spray tower whereby the spray tower may be located adjacent a wall of the test chamber and whereby test liquid will be blocked from exiting from the spray tower adjacent such test chamber wall.

The above objects are achieved in accordance with the present invention by providing a spray tower in the form of a vertical cylinder and wherein liquid is atomized and sprayed upwardly through the cylinder. A deflector is located at the upper end of the cylinder and deflects atomized test liquid outwardly therefrom to drop onto upwardly facing surfaces of test samples located within a test chamber. The cylinder has therein, in at least one vertically intermediate location, a plurality of ports spaced around the circumference of the cylinder. Located within the cylinder adjacent each group of ports is a directing member which directs a portion of the upwardly moving atomized test liquid outwardly through the ports and against irregularly configured surfaces of the test samples.

Attached to the exterior of the cylinder are shielding plates, for example of semi-cylindrical configuration. The shielding plates are vertically adjustably mounted on the cylinder so that they may be vertically moved between a closed or blocking position blocking a portion of the ports, and an open position unblocking such ports. There is also vertically adjustably attached to the exterior of the cylinder, adjacent the open upper end thereof, an uppermost shield plate which is vertically movable between an upper position blocking a portion of a gap formed between the open upper end of the cylinder and the deflector and a lowered position unblocking such gap. By the arrangement of these shielding plates, it is possible to prevent the liquid from existing from the spray tower over a certain portion of the periphery thereof, for example over approximately one-half the periphery when the shield plates are semi-cylindrical.

BRIEF DESCRIPTION OF THE DRAWINGS

Other objects, features and advantages of the present invention will be discussed in more detail below with reference to the attached drawings, wherein.

DETAILED DESCRIPTION OF THE INVENTION

Figure 1:
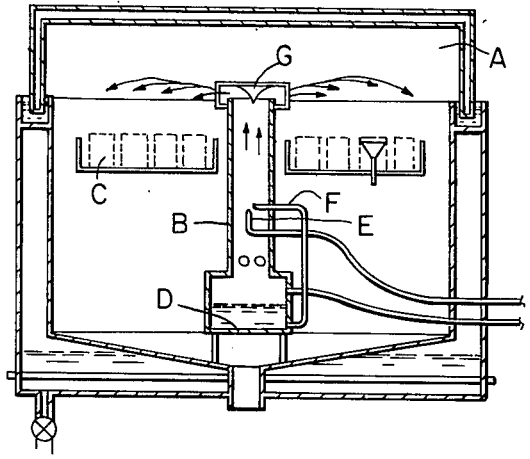
FIG. 1 is a sectional view of a conventional spray tower and test chamber arrangement for conducting liquid corrosion testing.

With reference now to FIG. 1 of the drawings, description will be made of a conventional spray tower to be used in a corrosion testing chamber for subjecting various objects and samples to liquid corrosion testing. In FIG. 1, as well as the other Figures of the drawings, it is to be understood that the relative sizes of various of the structural elements have been distorted for purposes of clarity of illustration.

In FIG. 1, a conventional spray tower B is suitably positioned within an enclosed chamber A of a conventional corrosion test chamber. A plurality of flat plate-like samples C to be tested are positioned within chamber A by any suitable means such as support frames. Liquid to be used in the corrosion test is supplied from a reservoir container D at the base of spray tower B and is ejected through a liquid nozzle F which extends substantially horizontally into a lower portion of spray tower B. The testing liquid which is ejected from nozzle F is atomized by air or other gas which is jetted from an air nozzle E. The atomized spray of test liquid then passes upwardly through spray tower B and is deflected by a deflector G positioned above spray tower B. The atomized spray is deflected by deflector G in the manner indicated by the arrows in FIG. 1 and drops onto the exposed top surfaces of the samples C.

Although the conventional spray tower described above with regard to FIG. 1 does a good job of covering the majority of surfaces of flat or plate-like samples, the conventional spray tower is not well suited for the corrosion testing of samples having complicated and irregular three-dimensional configurations. More specifically, in using the apparatus shown in FIG. 1, the test liquid is supplied directly only to the top surfaces of the samples. Any application of the test liquid to the side or other surfaces of a test sample will be due only to gravity flow of the test liquid. Thus, when the samples to be tested have a complicated or irregular shape, certain surfaces of such samples will never be subjected to the test liquid.

However, the above disadvantages of the conventional spray tower are overcome in accordance with the present invention. Specifically, and with reference now to FIG. 2 of the drawings, an improved spray tower according to the present invention includes a substantially vertically extending cylinder 5 extending upwardly from the center portion of a cover plate 6 of a liquid supply reservoir or container 3. Test liquid is supplied into container 3 via a liquid supply pipe 1 which may be operated in a conventional manner, for example by float valve 2. Liquid is supplied in a conventional manner from container 3 through liquid nozzle tube 16 and is ejected into cylinder 5 via liquid nozzle 16a. Air or other atomizing gas is supplied via air nozzle tube 17 in a conventional manner into the interior of cylinder 5 via air nozzle 17a. Air ejected from nozzle 17a atomizes the test liquid ejected through nozzle 16a, and the atomized test liquid then passes upwardly through cylinder 5.

A ring 11 is fixed about cylinder 5 at a position adjacent the upper end thereof. At least one rod or column 12 extends upwardly from ring 11. Column or columns 12 support a spray deflector 13 which has an upwardly and outwardly conically curved surface. The vertical position of deflector 13 with respect to column or columns 12 is adjustable, such that the vertical position of deflector 13 relative to cylinder 5 is adjustable. Such adjustment may be achieved by any conventional mechanical expedient.

Figure 4:
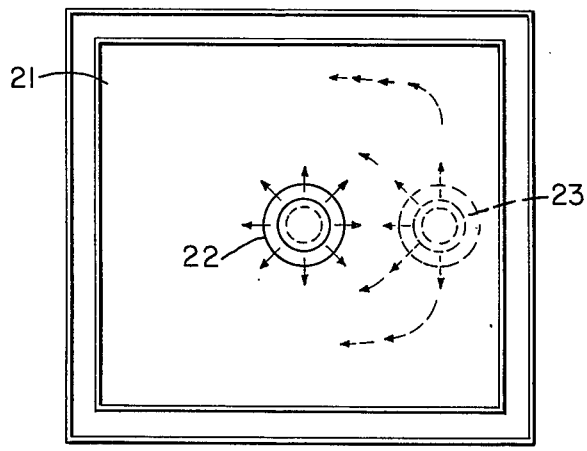
FIG. 4 is a schematic plan view illustrating various manners of positioning the spray tower of FIG. 2 within a testing chamber and the resultant spray patterns achievable thereby.
Figure 5:
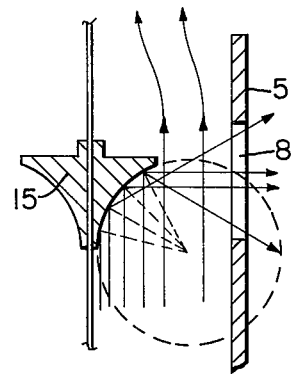
FIG. 5 is an enlarged sectional view schematically illustrating the flow of atomized liquid with respect to spray deflecting members positioned within the tower of FIG. 2.
Figure 6:
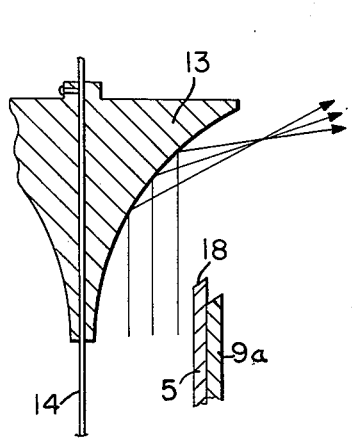
FIG. 6 is a view similar to FIG. 5 but schematically illustrating the flow of atomized liquid with respect to an uppermost deflector of the spray tower of FIG. 2.
Figure 7:
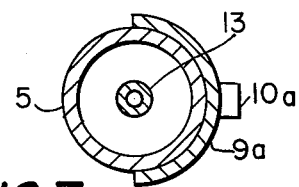
FIG. 7 is a cross-sectional view taken along line VII—VII of FIG. 2.

Deflector 13 has depending centrally downwardly therefrom a support rod 14 which supports thereon at least one supplemental deflector or directing member 15 within the interior of cylinder 5. In the illustrated embodiment, two such directing members 15 are shown. However, it is to be understood that the scope of the present invention includes the provision of only one or more than two such directing members 15. The directing members 15 have a diameter smaller than the inner diameter of cylinder 5 and are provided to deflect a portion of the atomized spray passing upwardly through cylinder 5 through atomizing ports 8 extending through cylinder 5 at positions spaced along the length thereof adjacent respective of the directing members 15. That is, in the illustrated embodiment there are provided ports 8 at two different vertical positions of cylinder 5. At each such vertical position of cylinder 5 there are provided a plurality of ports extending through cylinder 5 at positions spaced circumferentially therearound. In the illustrated embodiment, as particularly shown in FIGS. 8 and 9 of the drawings, each such vertical position includes eight ports 8. However, it is again to be understood that the scope of the present invention is not specifically limited to this number and that fewer or greater ports 8 may be provided at each vertical position.

As shown in FIG. 2 of the drawings, a ventilation port 7 is provided adjacent the bottom of cylinder 5 to allow the introduction of air therethrough to smooth the flow of atomizing liquid within cylinder 5.

As further shown in FIG. 2 of the drawings, liquid nozzle tube 16 may have on the end thereof within container 3 a filter 19 to filter the liquid passing from container 3 into nozzle tube 16.

As still further shown in FIG. 2 of the drawings, and as also shown in FIG. 6, the upper edge 18 of cylinder 5 may be tapered inwardly and downwardly to prevent the accumulation of liquid thereon.

With reference now to FIG. 5 of the drawings, each directing member 15 has an upwardly and outwardly conically tapered surface which confronts the upwardly moving atomized test liquid. The curvature of the curved deflecting surface of directing member 15, taken in vertical axial section, is a portion of the periphery of a circle, as shown by dashed lines in FIG. 5.

The diameters of directing members 15 are less than the inner diameter of cylinder 5 and are suitably selected and dimensioned such that the atomized test liquid passing upwardly through the cylinder 5 may be metered and distributed among the various groups of ports 8 and the upper outlet end of cylinder 5. For example, in the embodiment illustrated, it may be desired to establish the diameters of the lower and upper directing members 15 such that one-third of the atomized test liquid is distributed through each of the lower group of ports 8, the upper group of ports 8 and the upper outlet end of the cylinder 5.

Furthermore, directing members 15 may be positioned adjustably with respect to rod 14, and/or rod 14 may be adjustably positioned with respect to deflector 13, so that the relative heights of directing members 15 with respect to the adjacent ports 8 may be adjusted, thereby adjusting the spread of atomizing test liquid emitted from each group of ports 8.

With reference now to FIG. 6 of the drawings, deflector 13 has a diameter larger than that of cylinder 5, and the atomized liquid is deflected by the curved surface thereof to flow obliquely upwardly and then downwardly. The rate of spraying performed through the top of the cylinder 5 may be adjusted by varying the gap between the peripheral edge 18 of the top of the cylinder 5 and the deflector 13. This adjustment is achieved in the manner discussed above, i.e. by the relative position of deflector 13 and column 12 or of column 12 and ring 11.

With reference now to FIG. 4 of the drawings, various spray patterns within a chamber 21 of a test chamber will be described. For instance, in the position shown at 22 in FIG. 4, the spray tower is located substantially centrally within chamber 21. In this arrangement, test samples would be located all around the test tower, and it would be desired that the spray of test liquid from the tower be in all directions.

However, it is sometimes desired to place the spray tower adjacent a wall of the test chamber, as indicated by reference numeral 23 in FIG. 4. This may be the situation for example when several test towers are arranged within the test chamber. In the position illustrated by spray tower 23 in FIG. 4, it is necessary and desirable for test liquid to be sprayed from only approximately half of the spray tower. That is, any liquid which is sprayed from the right side of spray tower 23 will only be directed against the wall of the test chamber and will not serve any useful testing purpose.

Therefore, in accordance with a further advantageous feature of the present invention, the spray tower is provided with shield plates 9 which are selectively positionable to block off a portion of the ports 8.

Figure 2:
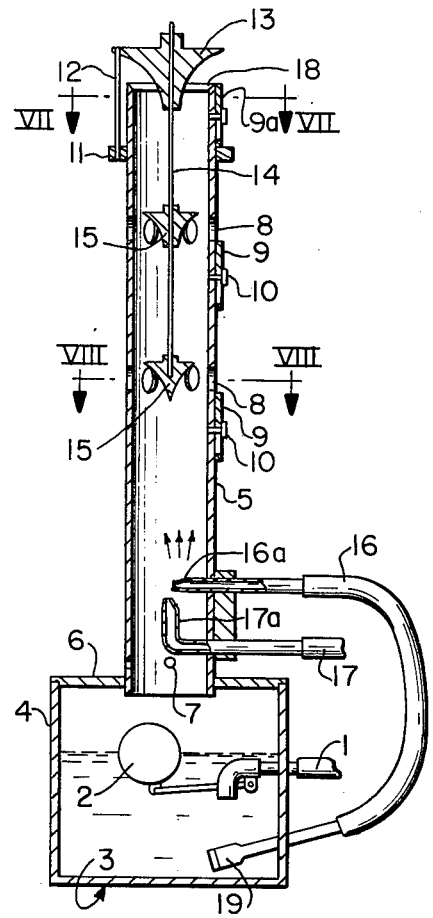
FIG. 2 is a sectional view of a spray tower in accordance with the present invention for achieving three-dimensional spraying within a corrosion testing chamber.
Figure 8:
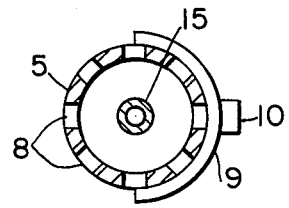
FIGS. 8 and 9 are cross-sectional views taken along line VIII—VIII of FIG. 2, and showing the shielding plate members thereof in the lowered and raised positions, respectively.
Figure 9:
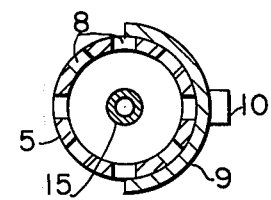
Figure 10:
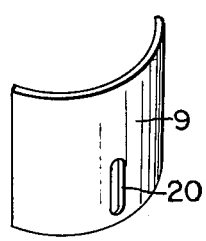
FIG. 10 is a perspective view of a shielding plate member used in the spray tower of FIG. 2.

Specifically, and as shown in FIG. 2 of the drawings, a shield plate 9 is adjustably attached to cylinder 5 adjacent each group of ports 8. Specifically, each shield plate 9 has a vertical slot 20 therein, and a fastener such as bolt 10 extends through slot 20 into the wall of cylinder 5. Thus, shield plates 9 may be adjustably vertically positioned along the exterior of cylinder 5 to selectively open or block a portion, for example one-half, of the ports 8. In FIGS. 2 and 8 of the drawings, shield plates 9 are in their lowered positions such that all of ports 8 are exposed. The spray pattern under this arrangement would be as shown by spray tower 22 in FIG. 4 of the drawings. However, in FIG. 9 of the drawings, the shield plates 9 are raised to block half of the ports 8. In this position, the spray pattern would be as shown by spray tower 23 in FIG. 4.

Additionally, an uppermost shield plate 9a is adjustably attached to cylinder 5 adjacent the open upper end thereof. Uppermost shield plate 9a is adjustably mounted by means of a fastener such as a bolt 10a, in the same manner as shield plates 9. Uppermost shield plate 9a is movable between the lower position shown in FIG. 2 of the drawings to an upper, blocking position blocking a portion of the gap between the open upper end of the cylinder and the deflector member 13. This thereby prevents liquid from passing outwardly through a portion of the upper end of the cylinder, for example as illustrated schematically by spray tower 23 in FIG. 4.

It is to be specifically understood that although in the illustrated embodiment the shield plates 9 extend around approximately half of the circumference of cylinder 5, shield plates 9 could be designed to extend around less than half or more than half of the circumference of cylinder 5.

Figure 3:
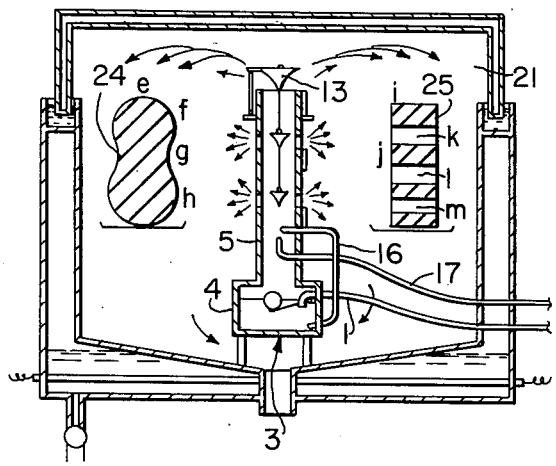
FIG. 3 is a sectional view of the spray tower of FIG. 2 positioned within a corrosion testing chamber for conducting corrosion tests on variously irregularly configured test sample articles.

With reference now to FIG. 3 of the drawings, the operation and advantages of the present invention will be discussed in more detail. Thus, in FIG. 3 there are shown test samples 24 and 25 of different irregular configurations positioned within chamber 21 of a conventional test chamber. The spray tower of FIG. 2 is positioned within chamber 1 and is operated in the manner described above to spray test liquid through two levels of intermediate ports 8 and through the upper end of cylinder 5. Shield plates 9 are lowered such that the test liquid is sprayed through all of ports 8.

Reference letters e, f, g and h illustrate various different surfaces of test sample 24. Similarly, reference letters i, j, k, l and m represent various surfaces of test sample 25. As will be apparent from the uppermost arrows in FIG. 3, the uppermost portions e and i of test samples 24 and 25, respectively, will be readily sprayed with test liquid exiting from the upper end of cylinder 5.

However, due to the provision of ports 8 and directing members 15, the surface portions f, g and h of test sample 24 and j, k, l and m of test sample 25 will also be covered with the test liquid. Such samples would not be covered, or at best would only partially be covered, by employing the conventional spray tower shown in FIG. 1.

The direction and rate of flow of the various sprays may be adjusted as discussed above.

It will be apparent from the above discussion that the use of the novel spray tower of the present invention makes it possible to cover a much greater portion of the surfaces of irregularly configured test samples than would be possible by use of a conventional spray tower. It is thereby possible to achieve more realistic and desired test results.

It will be further apparent from the above discussion that in accordance with the present invention it is possible to employ more than a single spray tower in a test chamber and/or to locate the spray tower adjacent a wall of the test chamber, without the need for wasting test liquid. Specifically, the provision of adjustable shield plates 9 makes it possible to close certain of the ports, thereby preventing the wasting of test fluid which would otherwise not be directed toward test samples.

It will be apparent that various modifications may be made to the above specifically described structural arrangements without departing from the scope of the present invention.

What is claimed is:

1. A spray tower for use in spraying a liquid material, said spray tower comprising:
 a vertically extending cylinder having an open upper end;
 means for injecting a liquid into said cylinder adjacent a lower portion thereof;
 means for atomizing said liquid injected into said cylinder and for passing the thus atomized liquid upwardly through said cylinder toward said open upper end thereof;
 said cylinder having ports extending therethrough in at least one position intermediate said open upper end and said atomizing means;
 deflector means, mounted above said open upper end of said cylinder, for deflecting outwardly atomized liquid exiting from said open upper end; and
 directing means, mounted within said cylinder adjacent said ports, for directing a portion of the atomized liquid passing upwardly through said cylinder outwardly through said ports.

2. A spray tower as claimed in claim 1, further comprising a liquid reservoir positioned at the bottom of said cylinder, and wherein said injecting means comprises a liquid nozzle extending into said cylinder and a liquid nozzle tube extending from said reservoir to said liquid nozzle, and said atomizing means comprises a gas nozzle extending into said cylinder and directed toward liquid exiting from said liquid nozzle and a gas nozzle tube connecting said gas nozzle to a source of pressurized gas.

3. A spray tower as claimed in claim 1, wherein said ports comprise a plurality of ports spaced circumferentially around said cylinder.

4. A spray tower as claimed in claim 1, wherein said ports comprise plural groups of ports, each of said group of ports being located at a different vertical position of said cylinder and including a plurality of ports spaced circumferentially around said cylinder.

5. A spray tower as claimed in claim 1, further comprising means for selectively blocking a portion of said ports to prevent the passage therethrough of said atomized liquid.

6. A spray tower as claimed in claim 5, wherein said blocking means comprises at least one shield plate, and means for adjustably vertically attaching said shield plate to said cylinder such that said shield plate is vertically movable between a blocking position covering a portion of said ports and an open position wherein all of said ports are unblocked.

7. A spray tower as claimed in claim 6, wherein said shield plate is semi-cylindrical.

8. A spray tower as claimed in claim 6, wherein said ports comprise plural groups of ports, each of said group of ports being located at a different vertical position of said cylinder and including a plurality of ports spaced circumferentially around said cylinder, one of said shield plates being attached to said cylinder adjacent each of said groups of ports.

9. A spray tower as claimed in claim 6, further comprising an uppermost shield plate vertically adjustably attached to said cylinder adjacent said open upper end thereof, said uppermost shield plate being vertically movable between an upper position blocking a portion of a gap between said open upper end of said cylinder and said deflecting means and a lower position unblocking said gap.

10. A spray tower as claimed in claim 9, wherein said uppermost shield plate is semi-cylindrical.

11. A spray tower as claimed in claim 1, wherein said directing means comprises at least one directing member having an upwardly and outwardly conically tapered surface which confronts and deflects a portion of the upwardly moving atomized liquid.

12. A spray tower as claimed in claim 11, wherein the curvature of said surface of said directing member, taken in vertical axial section, is a portion of the periphery of a circle.

13. A spray tower as claimed in claim 11, wherein the diameter of said directing member is less than the inner diameter of said cylinder.

14. A spray tower as claimed in claim 11, wherein said ports comprise plural groups of ports, each of said group of ports being located at a different vertical position of said cylinder and including a plurality of ports spaced circumferentially around said cylinder, one of said directing members being positioned within said cylinder adjacent each of said groups of ports.

15. A spray tower as claimed in claim 14, wherein the vertical position of each of said directing members with respect to the respective said group of ports is adjustable.

16. A spray tower as claimed in claim 11, wherein said deflecting means comprises a deflector member having an upwardly and outwardly conically curved surface which confronts and deflects the atomized liquid passing outwardly through said open upper end of said cylinder.

17. A spray tower as claimed in claim 16, wherein the diameter of said deflector member is greater than the inner diameter of said cylinder.

18. A spray tower as claimed in claim 16, wherein the vertical position of said deflector member with respect to said cylinder is adjustable.

19. A spray tower as claimed in claim 16, further comprising at least one column supporting said deflector member, said column being mounted on said cylinder.

20. A spray tower as claimed in claim 16, wherein said deflector member has depending downwardly therefrom a support rod, said support rod extending into the interior of said cylinder, said directing member being mounted on said support rod.

21. A spray tower as claimed in claim 1, wherein said deflecting means comprises a deflector member having an upwardly and outwardly conically curved surface which confronts and deflects the atomized liquid passing outwardly through said open upper end of said cylinder.

22. A spray tower as claimed in claim 21, wherein the diameter of said deflector member is greater than the inner diameter of said cylinder.

23. A spray tower as claimed in claim 21, wherein the vertical position of said deflector member with respect to said cylinder is adjustable.

24. A spray tower as claimed in claim 21, further comprising at least one column supporting said deflector member, said column being mounted on said cylinder.

25. A spray tower as claimed in claim 1, wherein the upper edge of said cylinder is inwardly and downwardly tapered.

* * * * *